United States Patent
Bessa Bellmunt et al.

(10) Patent No.: US 6,388,134 B1
(45) Date of Patent: May 14, 2002

(54) DERIVATIVES OF 6-(4-PHENYLBUTOXY) HEXYLAMINE AND PROCESS FOR PRODUCING SALMETEROL

(76) Inventors: Jordi Bessa Bellmunt, C. Corsega, 397, E-08037 Barcelona; Pere Dalmases Barjoan, C. Pi i Margall, 7, E-08980 Sant Feliu Del Llobregat; Francisco Marquillas Olondriz, Maria Auxilliadora, 19, 08017 Barcelona, all of (ES)

( * ) Notice: Subject to any disclaimer, the term of this patent is extended or adjusted under 35 U.S.C. 154(b) by 0 days.

(21) Appl. No.: 09/806,538
(22) PCT Filed: Sep. 20, 1999
(86) PCT No.: PCT/ES99/00294
§ 371 Date: Mar. 28, 2001
§ 102(e) Date: Mar. 28, 2001
(87) PCT Pub. No.: WO00/18722
PCT Pub. Date: Apr. 6, 2000

(30) Foreign Application Priority Data

Sep. 28, 1998 (ES) .................................. P 9802014

(51) Int. Cl.⁷ .............................................. C07C 213/00
(52) U.S. Cl. ........................................ 564/346; 560/29
(58) Field of Search ............................. 560/29; 564/346

(56) References Cited

FOREIGN PATENT DOCUMENTS

| EP | 0162576 | * | 11/1985 |
| ES | 2065269 | * | 2/1995 |
| FR | 2545482 | * | 11/1984 |

* cited by examiner

Primary Examiner—Samuel Barts
(74) Attorney, Agent, or Firm—Steinberg & Raskin, P.C.

(57) ABSTRACT

The present invention refers to new derivatives of the 6-(4-phenylbutoxy)hexylamine of the general formula (I):

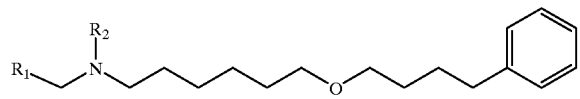

wherein:

$R_1$ is CHO or $CHOR_3OR_4$, where $R_3$ and $R_4$ independently are $C_1$–$C_6$ alkyl, aralkyl, or they form 5 or 6 membered cyclic acetals; and $R_2$ is H, benzyl or an alkyloxycarbonyl, aryloxycarbonyl, aralkyloxycarbonyl or acyl group;

and to a process for its obtention. The invention also refers to a new process for obtaining Salmeterol or its pharmaceutically acceptable salts, characterized in that reaction of an organometallic compound of the general formula (13) is carried out in an inert solvent at low temperature with a synthetic intermediate of the general formula (I), wherein $R_1$ is CHO, and $R_2$ is an alkyloxycarbonyl, aryloxycarbonyl, aralkyloxycarbonyl or acyl group.

38 Claims, No Drawings

DERIVATIVES OF 6-(4-PHENYLBUTOXY) HEXYLAMINE AND PROCESS FOR PRODUCING SALMETEROL

FIELD OF THE INVENTION

The present invention refers to novel 6-(4-phenyl-butoxy) hexylamine derivatives of the general formula (I) as well as to a process for the obtention thereof. The invention also refers to a process for the obtention of Salmeterol from said novel derivatives.

The novel 6-(4-phenylbutoxy)hexylamine derivatives are represented by the general formula (I):

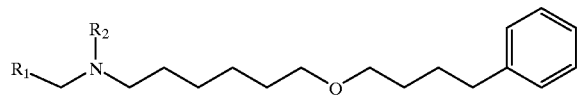

(I)

wherein:

$R_1$ is CHO or $CHOR_3OR_4$, where $R_3$ and $R_4$ independently are $C_1$–$C_6$ alkyl, aralkyl or they form 5 or 6 membered cyclic acetals; and $R_2$ is H, benzyl or an alkyloxycarbonyl, aryloxycarbonyl, aralkyloxycarbonyl or acyl group.

Said derivatives are useful as intermediates in the synthesis of Salmeterol.

BACKGROUND OF THE INVENTION

It is known the use of Salmeterol in the therapeutical field and specially for the treatment of asthma because of its properties as a bronchodilator. Several references may be found in the literature which describe processes for the obtention of Salmeterol.

Thus, Patent FR 2545482 discloses the following procedures for the obtention of Salmeterol:

By alkylation of an amine of the general formula 1 with an alkylating agent of the general formula 2:

1

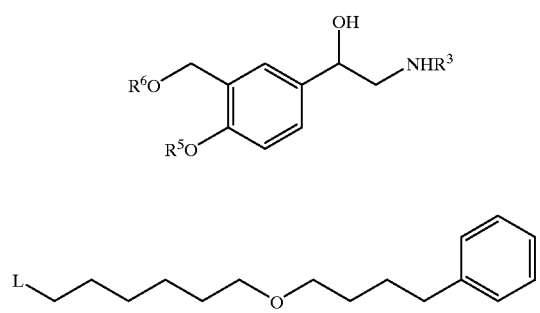

2 where $R^3$, $R^5$ and $R^6$ each represent a hydrogen atom or a protecting group, and L a leaving group as chlorine, bromine, iodine, mehanesufonyloxy or p-toluenesulfonyloxy and further removal of the eventually present protecting groups.

Alternatively, alkylation may be carried out by reductive amination of aldehyde 3 with amine 1 ($R_3$=H or a group convertible into H under the reaction conditions).

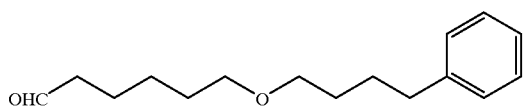

3

By reduction of a compound of the general formula 4:

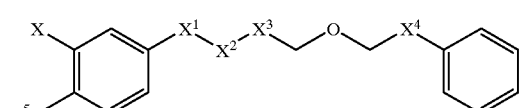

4 wherein $R^5$ is a hydrogen atom or a protecting group, and at least one of the X, $X^1$, $X^2$, $X^3$ and $X^4$ radicals is a reducible group; and further removal of the eventually present protecting groups.

Suitable reducible groups are:

X : COOH or $COOR^7$ (where $R^7$ is H, alkyl, aryl or aralkyl), and CHO.

$X^1$: C=O.

$X^2$: $CH_2NY$ (where Y is convertible into H by hydrogenation), CH=N and CONH.

$X^3$: $CO(CH_2)_5$, CH=CH—$(CH_2)_4$, $CH_2CH$=$CH(CH_2)_3$, etc.

$X^2$—$X^3$: $CH_2N$=CH $(CH_2)_5$.

$X^4$: CH=CH($CH_2$ )$_2$, $CH_2CH$=$CHCH_2$, etc.

By reaction of epoxide 5 or halohydrine 6 with the amine 7:

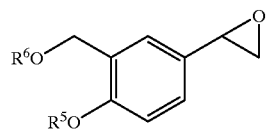

5

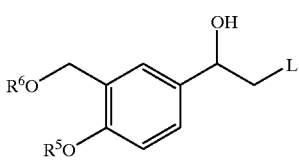

6

7

Y$^1$NH~~~~~~O~~~ where $Y^1$ is H or a group convertible into hydrogen by hydrogenation; and further removal of the eventually present protecting groups.

On the other hand, Patent WO 9824753 discloses an asymmetric synthesis of amine 10 and its application to the synthesis of optically active Salmeterol.

The asymmetric addition of nitromethane to the aldehyde 8 affords the optically active nitroderivative 9, the reduction of which leads to amine 10.

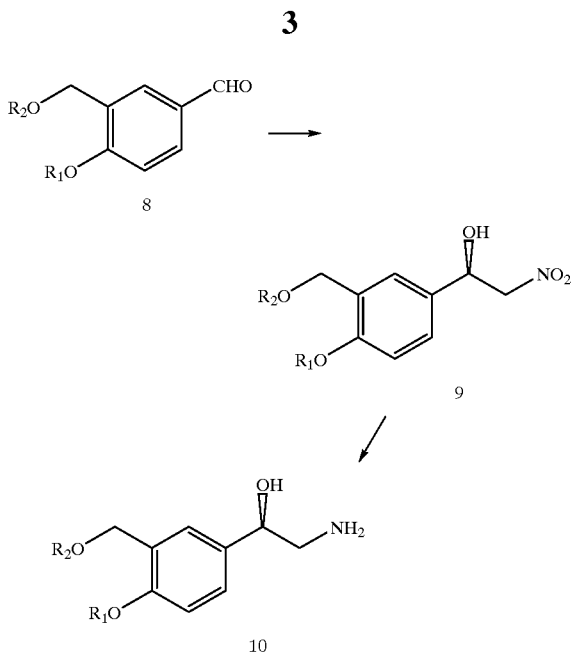

where $R_1$ and $R_2$ are suitable protecting groups.

However, these procedures described in the prior art present some drawbacks. The starting compounds are highly functionalized low-molecular weight intermediates, whereby its obtention involves considerably complex reactions, specially at industrial level, mainly due to the formation of undesirable byproducts which, moreover, decrease the yield of the reaction.

Thus, for example, the obtention of said compound 1 (GB 1200886) comprises many steps, among them, a bromination reaction and a chloromethylation, with the ensuing possibility of formation of dibrominated derivatives and isomers, respectively.

On the other hand, halohydrine 6 is a very slightly stable compound and it is difficult to isolate due to its tendency to convert into epoxide 5 under basic conditions. Reactions for obtention of epoxides are neither simple, the use of epoxide 5 also presenting the additional drawback that the obtention of Salmeterol is effected by opening of the epoxide, which reaction is little advisable because of the obtention of many byproducts (Randall et al., *Tetrahedron Letters*, (1986), 2451–2454).

The present invention provides novel 6-(4-phenylbutoxy) hexylamine derivatives which are useful as starting compounds in a new procedure of obtention of Salmeterol. Said new derivatives are easily obtained from industrially available compounds by means of simple reactions such as hydrolysis or alkylation of alcohols or amines.

DESCRIPTION OF THE INVENTION

The present invention refers to novel 6-(4-phenylbutoxy) hexylamine derivatives of the general formula (I):

(I)

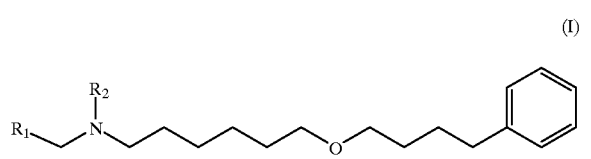

wherein:

$R_1$ is CHO or $CHOR_3OR_4$, where $R_3$ and $R_4$ independently are $C_{1-C6}$ alkyl, aralkyl, or they form 5 or 6 membered cyclic acetals; and $R_2$ is H, benzyl or an alkyloxycarbonyl, aryloxycarbonyl, aralkyloxycarbonyl or acyl group.

When $R_1$ is CHO, $R_2$ preferably is alkyloxycarbonyl, aryloxycarbonyl, aralkyloxycarbonyl, or an acyl group.

Preferably, $R_2$ is tert-butoxycarbonyl, benzyloxycarbonyl or ethoxycarbonyl, acetyl, benzoyl or trifluoroacetyl; and $R_3$ and $R_4$ independently are methyl, ethyl, benzyl, or they form 1,2-dioxolanes or 1,3-dioxanes.

It is also an object of the present invention a process for the obtention of said 6-(4-phenylbutoxy)hexylamine derivative compounds. Said process is outlined in Scheme I below.

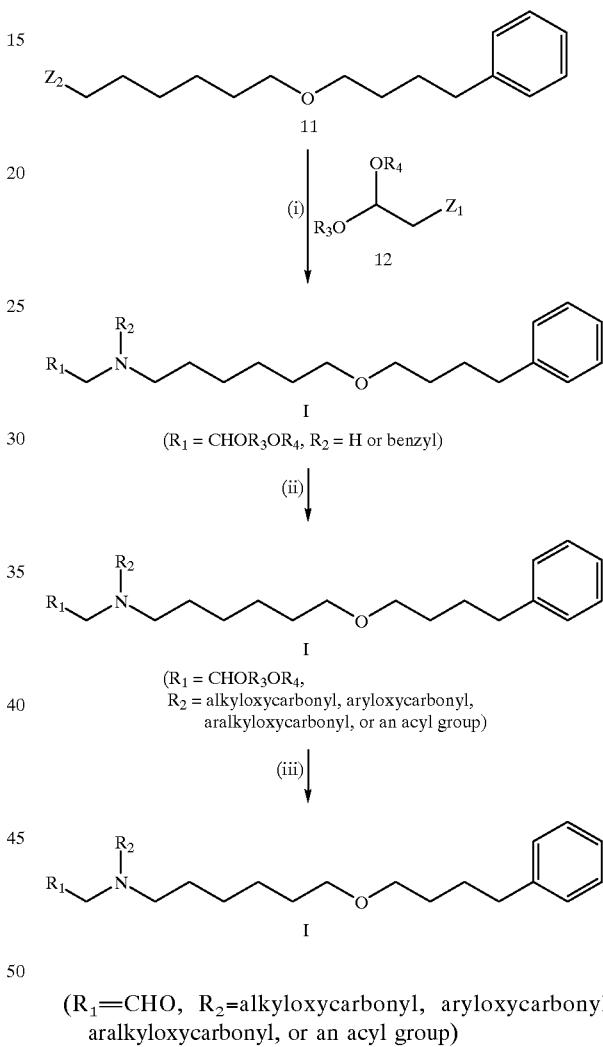

($R_1$=CHO, $R_2$=alkyloxycarbonyl, aryloxycarbonyl, aralkyloxycarbonyl, or an acyl group)

where:

$R_3$ and $R_4$ have the same meaning as described above;

$Z_1$ an $Z_2$ are each different and the same as L or $NHR_2$, L being a leaving group such as chlorine, bromine, iodine, methanesufonyloxy or p-toluenesulfonyloxy, preferably bromine; and $R_2$ is H or benzyl.

The process of obtention of said 6-(4-phenylbutoxy) hexylamine derivatives of the general formula (I) is carried out according to the following steps:

(i) Alkylation of an amine by reaction of a compound of the formula (11) with a compound of the formula (12) to yield a compound of the formula (I), with $R_1$=$CHOR_3OR_4$, $R_2$=H or benzyl:

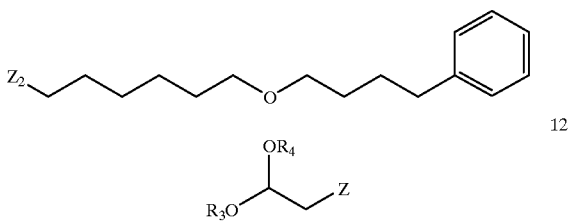

wherein:

R$_3$ and R$_4$ independently are C$_1$–C$_6$ alkyl, aralkyl, or they form 5 or 6 membered cyclic acetals;

Z$_1$ and Z$_2$ are each different and the same as L or NHR$_2$, where L is a leaving group such as chlorine, bromine, dine, methanesulfonyloxy or p-toluenesulfonyloxy; and R$_2$ H or benzyl;

in an inert solvent in the presence of an organic o organic base at a temperature ranging from 25° C. to 110° C., preferably from 80° C. to 100° C., to yield the compound of the general formula (I):

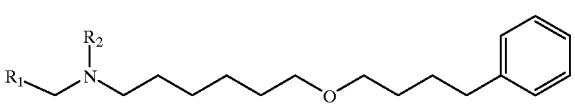

(I)

wherein R$_1$=CHOR$_3$OR$_4$ and R$_3$=H or benzyl.

The inert solvent may be a high boiling-point aprotic solvent such as, for example, N,N-dimethylformamide, N-methylpirrolidone or dimethylsulfoxide, an halogenated solvent such as methylene chloride or chloroform, an ether such as tetrahydrofuran or dioxane, or an aromatic hydrocarbon such as benzene, toluene or xylene.

The organic base may be a tertiary amine such as, for example, triethylamine or diisopropylethylamine, an aromatic amine such as N,N-dimethylaniline, or a heterocyclic amine such as pyridine. The inorganic base may be a carbonate or a bicarbonate.

(ii) Protection of the amino group of a compound (I) obtained in step (i) with a suitable reagent, prior to hydrogenation when R$_2$ is benzyl, which leads to the obtention of compounds of the formula (I), with R$_1$=CHOR$_3$OR$_4$, R$_2$ alkyloxycarbonyl, aryloxycarbonyl, aralkyloxycarbonyl, or an acyl group.

Referring to compounds of the formula (I) (when R$_1$=CHCOR$_3$OR$_4$, R$_2$=alkyloxycarbonyl, aryloxycarbonyl, aralkyloxycarbonyl, or an acyl group), R$_2$, R$_3$ and R$_4$ must be chosen so that it should exist the possibility of removing R$_3$ and R$_4$ without affecting R$_2$.

Protection of the amino group with the alkyloxycarbonyl, aryloxycarbonyl and aralkyloxycarbonyl residues is carried out by reaction of a compound of the formula (I), wherein R$_1$=CHOR$_3$OR$_4$, R$_2$=H, with a chloroformate such as, for example, ethyl chloroformate, tert-butyl chloroformate or benzyl chloroformate; a dicarbonate such as di-tert-butyl dicarbonate or dibenzyl dicarbonate; or specific reagents such as N-(benzyloxycarbonyl)succinimide. Protection with acyl groups is performed with conventional reagents such as acid chlorides or anhydrides.

The protection reaction is accomplished in an inert solvent, eventually in the presence of an organic or inorganic base, at a temperature ranging from 0° C. to 50° C.

The inert solvent may be a ketone as, for example, acetone; a halogenated derivative such as methylene chloride or chloroform; an ester such as, for example, ethyl acetate; an ether such as tetrahydrofuran or dioxane; or a high boiling- point solvent as N,N-dimethylacetamide or N,N-dimethylformamide.

The bases used for this reaction may be the same than the above mentioned ones when referring to step (i).

(iii) Conversion of the compound of the formula (I), obtained in step (ii), into the corresponding aldehyde by hydrolysis, transacetalization or hydrogenolysis of the acetal group, taking into account, when choosing the procedure, the compatibility with group R$_2$. Such conversion leads to the obtention of compounds of the formula (I), whit R$_1$=CHO, R$_2$=alkyloxycarbonyl, aryloxycarbonyl, aralkyloxycarbonyl, or an acyl group.

Hydrolysis is carried out in an organic solvent, in the presence of an at least stoichiometric amount of water and of an organic or inorganic acid such as hydrochloric, sulfuric, methanesulfonic, p-toluenesulfonic or trifluoroacetic acid, at a temperature preferably ranging from 15° C. to 50° C.

The solvent may be a ketone as acetone, an alcohol as methanol, ethanol or isopropanol, an amide as N,N-dimethylformamide or N,N-dimethylacetamide, etc.

Transacetalization is accomplished in the presence of a ketone such as, for example, acetone which at the same time acts as a solvent, and of an organic or inorganic acid as methanesulfonic, p-toluenesulfonic, hydrogen chloride or sulfuric, at a temperature preferably ranging from 15° C. to 50°C.

Hydrogenolysis is carried out under typical debenzylation conditions, in the presence of a catalyst in an inert solvent at a temperature ranging from 10° C. to 50° C. The catalyst preferably is palladium adsorbed on carbon.

The solvent may be a C$_1$ to C$_4$ aliphatic alcohol such as, for example, methanol, ethanol, isopropanol or butanol, an ester such as, for example, ethyl acetate, or an ether such as, for example, tetrahydrofuran.

The reaction temperature is preferably comprised between 15° C. and 25° C.

Compounds of the formula (I) obtained according to the above procedure are useful as intermediates in the synthesis of Salmeterol.

It is also an object of the present invention a process for the obtention of Salmeterol, or its pharmaceutically acceptable salts, from a compound of the general formula (I). Said procedure is characterized in that a reaction of an organometallic compound of the general formula (13) is carried out with a compound of the general formula (I):

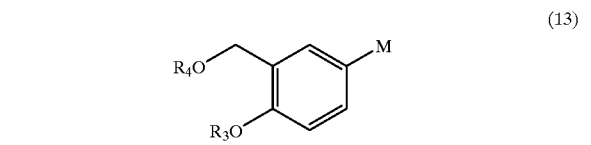

(13)

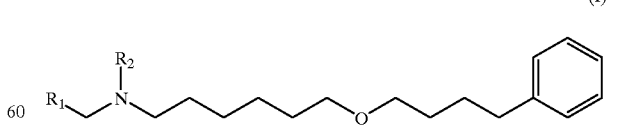

(I)

where:

R$_3$ and R$_4$ independently are C$_1$–C$_6$ alkyl, aralkyl, or they form cyclic acetals of the 1,3-dioxolane type;

M is a group containing a metal such as lithium, magnesium or copper, preferably M is Li, MgBr or MgCl; and $R_1$ is CHO and $R_2$ is an alkyloxycarbonyl, aryloxycarbonyl, aralkyloxycarbonyl or acyl group.

Preferably, $R_3$ and $R_4$ independently are methyl, ethyl or benzyl, or they form cyclic acetals such as 2,2-dimethyl-1,3-dioxane or 2-methyl-1,3-dioxane.

Preferably, $R_2$ is tert-butoxycarbonyl, benzyloxycarbonyl, ethoxycarbonyl, acetyl, benzoyl or trifluoroacetyl.

The reaction is carried out in an ether-like inert solvent, preferably ethyl ether or tetrahydrofuran at low temperatures preferably ranging from −40° C. to 40° C. and more preferably from −40° C. to 10° C.

The organometallic compound of the formula 13 may me obtained according to processes described in the literature (Effenberger, F.; Jäger, J., *J. Org. Chem.* (1977), 62, 3867–3873. Seebach, D., Neumann, H., *Chem. Ber.* (1974), 107, 874–853).

As shown in Scheme II, reaction of compound (I) with the organometallic 13 gives, after further hydrolysis, the alcohol 14, which, by subsequent removal of the protecting groups $R_2$, $R_3$ and $R_4$, leads to Salmeterol.

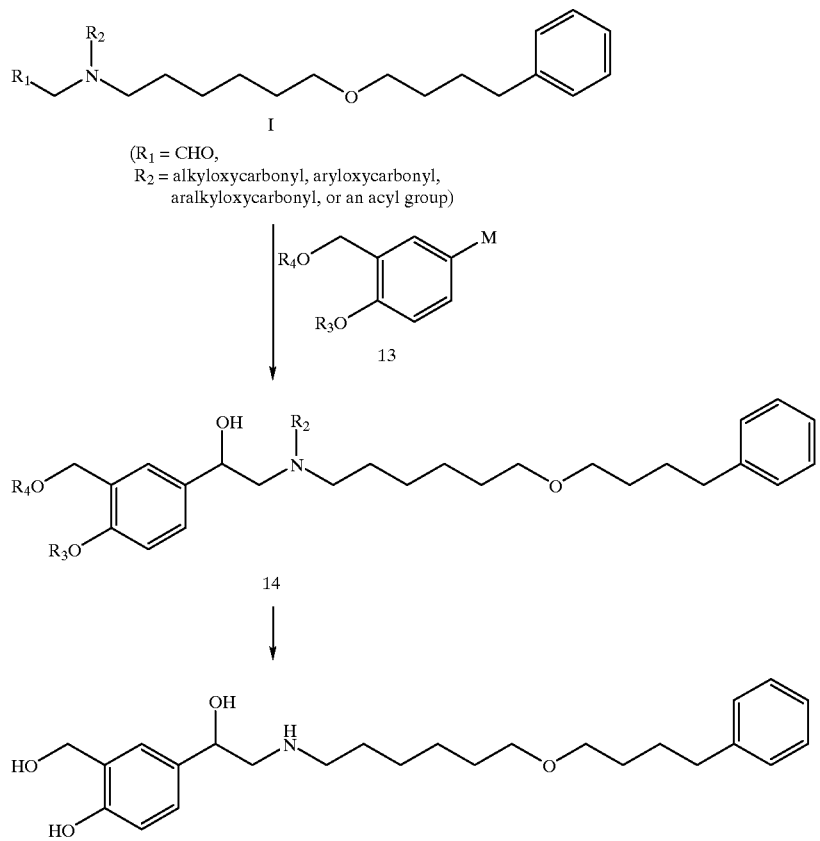

Salmeterol
where:
$R_3$ and $R_4$ independently are $C_1$–$C_6$ alkyl, aralkyl, or they form cyclic acetals of the 1,3-dioxane type such as 2,2-dimethyl-1,3-dioxane or 2-methyl-1,3-dioxane; and $R_2$ is an alkyloxycarbonyl, aryloxycarbonyl, aralkyloxycarbonyl or acyl group.

Isolation of alcohol 14 involves an aqueous treatment, in an acidic medium, of the crude product from the reaction.

Removal of the previously defined protecting groups $R_2$, $R_3$ and $R_4$ from compound of the formula 15 leads to Salmeterol. This stage may be performed in one or several steps. The reaction conditions depend upon the nature of the different protecting groups, and it may be carried out by acid or basic hydrolysis or by hydrogenolysis according to conventional methods (see, e.g.: "*Protective Groups in Organic Synthesis*", 2nd ed., John Wiley & Sons Ed., Inc. 1991).

Salmeterol may be converted into its pharmacologically acceptable addition salts, such as hydrochloride, fumarate, maleate or xynaphoate, following conventional procedures.

Experimental

EXAMPLE 1

4-(6-Bromohexyloxy)butylbenzene

To a mixture of 5 ml (32.75 mmol) 4-phenylbutanol with 10.1 ml (65.66 mmol) 1,6-dibromohexane is added 8 g (121.2 mmol) powdered KOH and 1.112 g (3.28 mmol) tetrabutylammonium hydrogen sulfate. After allowing the suspension to stir for 20 hr at room temperature, it is filtered and the filtrate dissolved in 50 ml $Et_2O$. The resulting solution is washed with water, dried on anhydrous $Na_2SO_4$, the $Et_2O$ evaporated and the residue distilled in vacuum (0.1 mmHg), a first fraction up to 100° C. of a mixture of starting products and a second fraction at 150° C. of 4-(6-bromohexyloxy)butylbenzene weighing 7.60 g (74.4 %) being collected.

RMN $^1H$ ($CDCl_3$), δ (ppm): 1.3–2.0 (m, 12H), 2.6 (t, 2H, —C$\underline{H}_2$—$C_6H_5$), 3.4 (m, 6H, —$CH_2$—O—$CH_2$—+—$CH_2Br$), 7.1–7.4 (m, 5H, —$C_6H_5$).

EXAMPLE 2

N-Dimethoxyethyl-6-(4-phenylbutoxy)hexylamine hydrobromide

To a solution of 8.7 ml (79.85 mmol) aminoacetaldehyde dimethylacetal in 60 ml toluene at reflux is added dropwise a solution of 10 g (31.94 mmol) 4-(6-bromohexyloxy)butylbenzene in 40 ml toluene. After maintaining the reaction mixture under reflux for 4 hr, toluene is evaporated off under reduced pressure, and 50 ml $CH_2Cl_2$ is added thereto. The resulting solution is stirred for 15 min together with a solution of 20 ml 47% HBr diluted with 20 ml $H_2O$. The reaction mixture is allowed to decant and the crude product obtained as a result of evaporating the $CH_2Cl_2$ phase to dryness is triturated with $Et_2O$ and filtered, thereby affording 4.31 g (32.3%) N-dimethoxyethyl-6-(4-phenylbutoxy)hexylamine hydrobromide.

RMN $^1H$ (CDCl$_3$), δ (ppm): 1.3 (m, 4H), 1.6 (m, 6H), 1.9 (m, 2H), 2.6 (t, 2H, —C$\underline{H}_2$—C$_6$H$_5$), 3.0 (m, 4H, —C$\underline{H}_2$—NH—C$\underline{H}_2$—), 3.4 (c, 4H, —CH$_2$—O—CH$_2$—), 3.45 (s, 6H, 2*CH$_3$), 4.95 (t, 1H, —C$\underline{H}$(OCH$_3$)$_2$), 7.1–7.3 (m, 5H, —C$_6$H$_5$).

EXAMPLE 3

N-Benzyl-6-(4-phenylbutoxy)hexylamine hydrobromide

A mixture comprising 7.34 g (25.53 mmol) 4-(6-bromohexyloxy)butylbenzene and 10.3 ml (94.30 mmol) benzylamine is heated at 125° C. for 8 hr. The benzylamine in excess is distilled off and the residue dissolved in 30 ml methyl ethyl ketone. To the resulting solution, heated to 50° C., is added a solution of 7.43 ml 47% HBr in 50 ml $H_2O$, then it is allowed to stir for 15 min and decanted. The organic phase is evaporated to dryness an the thus obtained residue triturated with $Et_2O$ and filtered to yield 5.9 g (59.8%) N-benzyl-6-(4-phenylbutoxy)hexylamine hydrobromide.

RMN $^1H$ (CDCl$_3$), δ (ppm): 1.2–2.0 (m, 12H), 2.6 (t, 2H, —C$\underline{H}_2$—C$_6$H$_5$), 2.8 (m, 2H, —NH—C$\underline{H}$—CH$_2$—), 3.35 (m, 4H, —CH$_2$—O—CH$_2$—), 4.05 (t, 2H, —NH—C$\underline{H}_2$—C$_6$H$_5$), 7.1–7.7 (m, 10H, 2*—C$_6$H$_5$), 9.35 (s, 2H).

IR (KBr, cm$^{-1}$): 2930, 2830, 2785, 1430, 1105, 750, 690.

EXAMPLE 4

6-(4-Phenylbutoxy)hexylamine

A solution of 4.02 g (11.86 mmol) N-benzyl-6-(4-phenylbutoxy)hexylamine in 40 ml EtOH is hydrogenated at room temperature and atmospheric pressure with 0.4 g 5% Pd/C. When 300 ml $H_2$ have been absorbed, the mixture is filtered on decalite and the filtrate is concentrated to yield 2.89 g (97.9%) 6-(4-phenylbutoxy)hexylamine as an oil.

RMN $^1H$ (CDCl$_3$), δ (ppm): 1.2–1.8 (m, 12H), 2.65 (c, 4H, —C$\underline{H}_2$—C$_6$H$_5$+—C$\underline{H}_2$NH$_2$), 3.4(c, 4H, —CH$_2$—O—CH$_2$—)7.1–7.4(m, 5H, —C$_6$H$_5$).

EXAMPLE 5

N-Benzyl-6-N-diethoyethyl-6-(4-phenylbutoxy)hexylamine

To 25 ml DMF is added 5 g (11.90 mmol) N-benzyl-6-(4-phenylbutoxy)hexylamine, 1.85 ml (11.93 mmol) bromoacetaldehyde diethylacetal and 3.29 g (23.84 mmol) $K_2CO_3$. The suspension is heated at 80° C. for 22 hr, after which time DMF is distilled off under reduced pressure. To the crude product is added 30 ml $CH_2Cl_2$ and the mixture is washed with 30 ml $H_2O$. After decanting the $CH_2Cl_2$, drying on anhydrous $Na_2SO_4$, concentrating to dryness and purifying by column chromatography on silica gel (gradient $CH_2Cl_2$ to $CH_2Cl_2$/AcOEt 9:1), it is obtained 2.25 g (51%) N-benzyl-N-diethyloxyethyl-6-(4-phenylbutoxy)hexylamine as an oil.

RMN $^1H$ (CDCl$_3$), δ (ppm): 1.2 (t, 6H, 2*—CH$_3$), 1.2–1.8 (m, 12H), 2.45 (t, 2H, —C$\underline{H}$—C$_6$H$_5$), 2.6 (m, 4H, —CH$_2$—N—CH$_2$—), 3.3–3.7 (m, 8H, —CH$_2$—O—CH$_2$—+2*—C$\underline{H}_2$—CH$_3$), 4.55 (t, 1H, —C$\underline{H}$(OCH$_2$CH$_3$)$_2$), 7.1–7.4 (m, 10H, 2*—C$_6$H$_5$).

EXAMPLE 6

N-Diethoyethyl-5-(4-phenylbutoxy)hexylamine

To a solution of 2.77 g (11.12 mmol) 6-(4-phenylbutoxy)hexylamine in 20 ml DMF is added 1.54 g (11.16 mmol) $K_2CO_3$ and 1.68 g (11.17 mmol) bromoacetaldehyde diethylacetal. After allowing the mixture to stand for 20 hr at 80° C., DMF is distilled off at reduced pressure, and the resulting crude product in 30 ml $CH_2Cl_2$ is washed with 30 ml $H_2O$. The $CH_2Cl_2$ phase is dried on anhydrous $Na_2SO_4$, concentrated to dryness and the residue is purified by column chromatography on silica gel (gradient $CH_2Cl_2$/AcOEt 1:1 to AcOEt), thereby yielding 1.73 g (42.6 %) N-diethoxyethyl-6-(4-phenylbutoxy)hexylamine as an oil.

Alternatively, 2,39 g (90,3 %) N-diethoxyethyl-6-(4-phenylbutoxy)hexylamine was also obtained by hydrogenation from a mixture of 3.24 g (7,53 mmol) N-benzyl-diethoxyethyl-6-(4-phenylbutoxy)hexylamine and 0.32 g 5% Pd/C in 35 ml EtOH, at room temperature and atmospheric pressure.

RMN $^1H$ (CDCl$_3$), δ (ppm): 1.2 (t, 6H, 2*CH$_3$), 1.25–1.8 (m, 12H), 2.6 (c, 2H, —C$\underline{H}_2$—C$_6$H$_5$), 2.7 (d, 1H, —NH—), 3.4 (c, 4H, 2* —OC$\underline{H}_2$CH$_3$), 3.5–3.8 (m, 4H, —CH$_2$—O—CH$_2$—), 4.6 (t, 1H, —C$\underline{H}$(OCH$_2$CH$_3$)$_2$), 7.1–7.3 (m, 5H, —C$_6$H$_5$).

EXAMPLE 7

N-Benzyloxycarbonyl-N-dimethoxyethyl-6-(4-phenylbutoxy)hexylamine

To a solution of 4.15 g (9.93 mmol) N-dimethoxyethyl-6-(4-phenylbutoxy)hexylamine hydrobromide in 40 ml acetone is added 1.4 ml triethylamine and 2.41 g (10.71 mmol) N-(benzyloxycarbonyloxy)succinimide. After allowing the mixture to stir for 2 hr at room temperature, acetone is evaporated of f and 40 ml $Et_2O$ is added thereto. The resulting mixture is washed three times with 40 ml $H_2O$. Once separated, the ether phase is dried on anhydrous $Na_2SO_4$ and evaporated to dryness, to yield 4.46 g (95.3%) N-benzyloxycarbonyl-N-dimethoxyethyl-6-(4-phenylbutoxy)hexylamine as an oil.

RMN $^1H$ (CDCl$_3$), δ (ppm): 1.2–1.8 (m, 12H), 2.65 (t, 2H, —C$\underline{H}_2$C$_6$H$_5$), 3.2–3.5 (m, 14H, 2*CH$_3$+—CH$_2$—N—CH$_2$—+—CH$_2$—O—CH$_2$—), 4.3–4.6 (dt, 1H, —C$\underline{H}$(OCH$_3$)$_2$), 5.15 (s, 2H, —O—C$\underline{H}_2$—C$_6$H$_5$), 7.1–7.4 (m, 10H, 2*C$_6$H$_5$).

EXAMPLE 8

N-Benzyloxycarbonyl-N-diethoxyethyl-6-(phenylbutoxy)hexylamine

To a solution of 2,39 g (6,55 mmol) N-diethoxyethyl-6-(4-phenylbutoxy)hexylamine in 25 ml acetone is added 1.59 g (7.07 mmol) N-(benzyloxycarbonyloxy)succinimide. After allowing the mixture to stir for 2 hr at room temperature, acetone is removed by evaporation and 30 ml AcOEt are added thereto. The resulting mixture is washed three times with 30 ml $H_2O$. Once separated, the AcOEt phase is dried on anhydrous $Na_2SO_4$ and evaporated to dryness, thereby yielding 3.28 g (99%) N-benzyloxycarbonyl-N-diethoxyethyl-6-(phenylbutoxy) hexylamine as an oil.

RMN $^1$H (CDCl$_3$), δ (ppm): 1.1–1.8 (m, 18H), 2.65 (t, 2H, —C$\underline{H}_2$—C$_6$H$_5$), 3.3–3.8 (m, 12H, 2*—O—C$\underline{H}_2$CH$_3$+—CH$_2$—N—CH$_2$—+—CH$_2$—O—CH$_2$—), 4.4–4.7 (dt, 1H, —C$\underline{H}$(OCH$_2$CH$_3$)$_2$), 5.15 (s, 2H, —O—C$\underline{H}_2$—C$_6$H$_5$), 7.1–7.4 (m, 10H, 2*—C$_6$H$_s$).

EXAMPLE 9

N-Benzyloxycarbonyl-N-(2-oxoethyl)-6-(4-phenylbutoxy)hexylamine

To a solution of 3,89 g (8,26 mmol) N-benzyloxycarbonyl-N-dimethoxethyl-6-(4-phenylbutoxy)hexylamine in 50 ml acetone is added p-toluenesulfonic acid monohydrate (0.786 g 4.13 mmol). After allowing the solution to stand at room temperature for 4 hr, acetone is evaporated off and the crude product dissolved in 50 ml Et$_2$O and washed once with 50 ml H$_2$O. The Et$_2$O phase is separated, dried on anhydrous Na$_2$SO$_4$, evaporated to dryness and the thus obtained residue purified by column chromatography on silica gel (gradient CH$_2$Cl$_2$ to CH$_2$Cl$_2$/AcOEt 4:1), thereby yielding 2.66 g (75.7 %) N-benzyloxycarbonyl-N-(2-oxoethyl)-6-(4-phenylbutoxy) hexylamine as an oil.

Alternatively, 1.66 g (72.3 %) N-benzyloxycarbonyl-N-(2-oxoethyl)-6-(4-phenylbutoxy)hexylamine could also be obtained from 2,70 g (5,41 mmol) N-benzyloxycarbonyl-N-diethoyethyl-6-(4-phenylbutoxy)hexylamine according to the above described method.

RMN $^1$H (CDCl$_3$), δ (ppm): 1.2–1.8 (m, 12H), 2.65 (t, 2H, —C$\underline{H}_2$—C$_6$H$_5$), 3.4 (m, 6H, —CH$_2$—N<, —CH$_2$—O—CH$_2$—), 4.0 (d, 2H, —O—C$\underline{H}_2$—C$_6$H$_5$) 5.15 (d, 2H, —C$\underline{H}_2$—CHO), 7.1–7.4 (m, 10H, 2*C$_6$H$_5$), 9.6 (d, 1H, —CHO).

EXAMPLE 10

2,2-Dimethyl-6-bromobenzo-1,3-dioxane

To a solution of 5.0 g (24.63 mmol) 3-bromo-6-hydroxybenzyl alcohol in 30 ml acetone cooled to 0° C., a solution of 1.15 g (8.62 mmol) AlCl$_3$ in 20 ml Et$_2$O is added dropwise. The resulting mixture is allowed to stand at room temperature for 1 hr, after which time it is cooled to 0° C. and 50 ml of a 10% NaOH aqueous solution previously cooled to 5° C. is added thereto. The separated Et$_2$O phase is washed twice with 20 ml H$_2$O, dried on anhydrous Na$_2$SO$_4$, evaporated to dryness and distilled under reduce pressure to yield 4.85 g (81%) 2,2-dimethyl-6-bromobenzo-1,3-dioxane as an oil.

RMN$^1$H(CDCl$_3$), δ (ppm)): 1.5(s, 6H, 2*CH$_3$), 4.8(s, 2H,—O—CH$_2$—), 6.7 (d, 1H), 7.1 (d, 2H), 7.25 (dd, 1H).

EXAMPLE 11

N-[2-(2,2-Dimethyl-4H-benzo[1,3]dioxin-6-yl)-2-hydroxyethyl]-N-benzyloxycarbonyl-6-(4-phenylbutoxy)hexylamine.

To 0.166 g (6.83 mmol) Mg in 1 ml THF is added dropwise a few drops of a solution comprising 1.51 g (6.21 mmol) 2,2-dimethyl-6-bromobenzo-1,3-dioxane in 20 ml THF and a catalytic amount of 1,2-dibromoethane. Once the reaction has started, the remaining 2,2-dimethyl-6-bromobenzo-1,3-dioxane solution was added while maintaining the temperature at 40° C. Upon completion of the addition (15 min), the reaction is allowed to stand a further 30 min at 40° C. The mixture is then cooled to −7° C. and a solution of 2.64 g (6.21 mmol) N-benzyloxycarbonyl-N-2-oxoethyl-6-(4-phenylbutoxy)hexylamine in 5 ml THF is added thereto. After allowing the reaction to stand at 0° C. for 1 hr, the temperature of the reaction mixture is allowed to increase to room temperature, 30 ml of a saturated NH$_4$Cl solution is added and the mixture stirred for 15 min. Finally, 30 ml AcOEt is added, the EtOAc phase is separated, washed with 30 ml H$_2$O, dried on anhydrous Na$_2$SO$_4$ concentrated to dryness and the residue purified by column chromatography on silica gel (gradient CH$_2$Cl$_2$ to CH$_2$Cl$_2$/EtOAc 4:1), to give 1.50 g (40.9%) N-[2-(2,2-dimethyl-4H-benzo[1,3]dioxin-6-yl)-2-hydroxyethyl]-N-benzyloxycarbonyl-6-(4-phenylbutoxy)hexylamine.

RMN $^1$H (CDCl$_3$), δ (ppm): 1.4–1.8 (m, 18H), 2.65 (t, 2H, —C$\underline{H}_2$—C$_6$H$_5$), 3.1–3.6(m, 9H), 4.8 (m, 3H, —C$\underline{H}$(OH)—, —CH$_2$—O—), 5.15 (s, 2H, —O—C$\underline{H}_2$—C$_6$H$_5$), 6.8 (d, 1H), 7.0–7.4 (m, 12H).

IR (KBr, cm$^{-1}$): 3430, 2930, 2860, 1695, 1500, 1265, 1120.

EXAMPLE 12

N-[2-(2,2-Dimethyl-4H-benzo[1,3]dioxin-6-yl)-2-hydroxyethyl]-6-(4-phenylbutoxy)hexylamine 0.9 g (1.53 mmol) N-[2-(2,2-dimethyl-4H-benzo[1,3]-dioxin-6-yl)-2-hydroxyethyl]-N-benzyloxycarbonyl-6-(4-phenylbutoxy)hexylamine is hydrogenated with 0.1 g 5% Pd/C in 30 ml MeOH at atmospheric pressure and room temperature. Once 50 ml H$_2$ have been absorbed, the catalyst is filtered off on decalite and the filtrate concentrated to dryness to give 0.69 g (99%) N-[2-(2,2-dimethyl-4H-benzo[1,3]dioxin-6-yl)-2-hydroxyethyl]-6-(4-phenylbutoxy) hexylamine.

RMN $^1$H (CDCl$_3$), δ (ppm)): 1.3–2.0 (m, 12H), 1.55 (s, 6H, 2*CH$_3$), 2.6 (t, 2H, —C$\underline{H}_2$—C$_6$H$_5$), 2.9–3.2(m, 4H, —CH$_2$—N—CH$_2$—), 3.35 (c, 4H, —CH$_2$—O—CH$_2$—), 4.8 (s, 2H, —CH$_2$—O—), 5.25 (dd, 1H, —C$\underline{H}$(OH)—), 6.75 (d, 1H), 7.05(d, 1H), 7.1–7.3 (m, 6H).

IR (KBr, cm$^{-1}$): 3355, 2930, 2855, 1630, 1595, 1490, 1260, 1120.

EXAMPLE 13

4-Hydroxy-al-[[[6-(4-phenylbutoxy)hexyl]amino]-methyl]-1,3-benzenedimethanol

To a solution of 0.6 g (1.32 mmol) [2-(2,2-dimethyl-4H-benzo[1,3]dioxin-6-yl)-2-hydroxyethyl]-6-[4-phenylbutoxy)hexylamine in 20 ml of a 1:1 H$_2$O/MeOH mixture is added 0.15 ml (1.75 mmol) 35% HCl. After allowing the reaction to stir for 48 hr at room temperature, the MeOH is evaporated off at reduced pressure. The resulting aqueous mixture is extracted with 20 ml CH$_2$Cl$_2$. The organic phase is washed sequentially with 20 ml of a saturated NaHCO$_3$ solution and further 20 ml H$_2$O, dried on anhydrous Na$_2$SO$_4$ and evaporated to dryness to yield 0.24 g (43.9%) 2-hydroxymethyl-4-{1-hydroxy-2-[6-(4-phenylbutoxy)hexylamino]ethyl}phenol.

RMN $^1$H (CDCl$_3$), δ (ppm)): 1.2–1.8 (m, 12H), 2.4–2.7 (m, 6H, —CH$_2$—N—CH$_2$—+—C$\underline{H}_2$—C$_6$H$_5$), 3.3–3.5 (m, 4H, —CH$_2$—O—CH$_2$—), 4.4–4.6 (m, 3H, —CH$_2$—OH+—CH(OH)—), 5.1 (s, 4H, 3*OH+NH), 6.7 (d, 1H), 6.8–7.0 (m, 2H), 7.1–7.3 (m, 5H, —C$_6$H$_5$).

What is claimed is:

1. A 6-(4-phenylbutoxy)hexylamine derivative compound of the general formula (I):

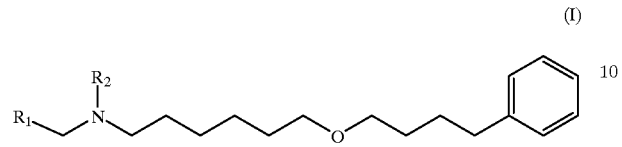

wherein:
R$_1$ is CHO or CHOR$_3$OR$_4$, where R$_3$ and R$_4$ independently are C$_1$–C$_6$ alkyl, aralkyl, or they form 5 or 6 membered cyclic acetals; and
R$_2$ is H, benzyl or an alkyloxycarbonyl, aryloxycarbonyl, aralkyloxycarbonyl or acyl group.

2. A compound as claimed in claim 1 characterized in that R$_1$ being equal to CHO, R$_2$ is an alkyloxycarbonyl, aryloxycarbonyl, aralkyloxycarbonyl or acyl group.

3. A compound as claimed in claim 1, characterized in that R$_3$ and R$_4$ independently are methyl, ethyl, benzyl, or they form either 1,3-dioxolanes or 1,3-dioxanes.

4. A compound as claimed in any one of claim 1 or 2, characterized in that R$_2$ is tert-butoxycarbonyl, benzyloxycarbonyl, ethoxycarbonyl, acetyl, benzoyl or trifluoroacetyl.

5. A process for the obtention of Salmeterol or its pharmaceutically acceptable salts, characterized in that reaction of an organometallic compound of the general formula (13) is carried out in an inert solvent at low temperature with a synthetic intermediate of the general formula (I):

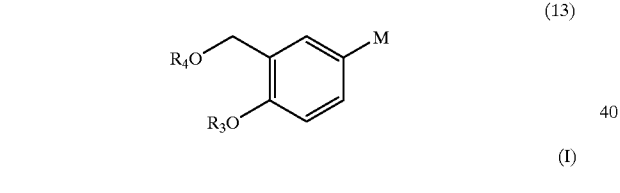

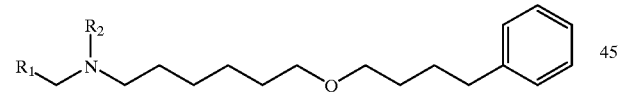

wherein:
R$_1$ and R$_4$ independently are C$_1$–C$_6$ alkyl, aralkyl, or they form cyclic acetals of the 1,3-dioxolane type;
M is a group containing a metal selected from lithium, magnesium or copper; and
R$_1$ is CHO, and R$_2$ is an alkyloxycarbonyl, aryloxycarbonyl, aralkyloxycarbonyl or acyl group;
followed by hydrolysis and removal of the protecting groups.

6. A process as claimed in claim 5, wherein said inert solvent is an ether.

7. A process as claimed in claim 5, characterized in that said reaction is carried out at a temperature ranging from −40° C. to 40° C., preferably from −40° C. to 10° C.

8. A process as claimed in claim 5, characterized in that R$_3$ and R$_4$ independently are methyl, ethyl, benzyl, 2,2-dimethyl-1,3-dioxane or 2-methyl-1,3-dioxane.

9. A process as claimed in claim 5, characterized in that M is Li, MgBr or MgCl.

10. A process for obtaining a 6-phenyl-butoxy)hexylamine derivative compound of the general formula (I) as claimed in claim 1, wherein the following steps are performed:
(i) alkylizing an amine by reaction of a compound of the formula (11) with a compound of the formula (12)

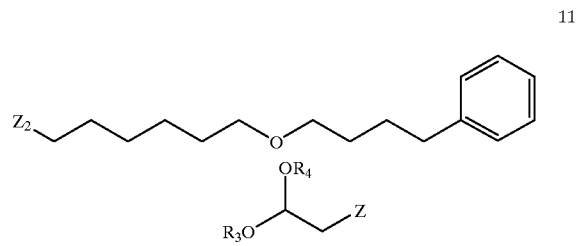

wherein:
R$_3$ and R$_4$ independently are C$_1$–C$_6$ alkyl, aralkyl, or they form 5 or 6 membered cyclic acetals; and
Z$_1$ and Z$_2$ are each different and the same as L or NHR$_2$, being a leaving group wherein said leaving group is selected from a group consisting essentially of chlorine, bromine, iodine, methanesulfonyloxy and p-toluene-sulfonyloxy; and R$_2$ is H or benzyl;
in an inert solvent in the presence of an organic or inorganic base at a temperature ranging from 25 to 110° C., to yield the compound of the general formula (I)

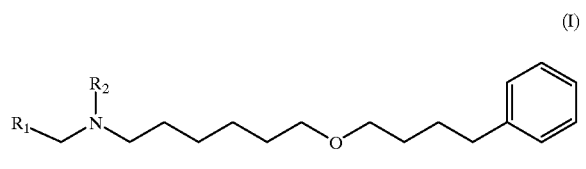

wherein R$_1$ is CHOR$_3$OR$_4$, and R$_3$ is H or benzyl;
(ii) protecting the amino group of the compound obtained in step (i) with a suitable reagent, with previous hydrogenation when R$^2$ is benzyl, in an inert solvent, optionally in the presence of an organic or inorganic base, at a temperature ranging from 0° C. to 50° C., for obtaining the compound of the formula (I) where R$_1$=CHOR$_3$OR$_4$ and R$_2$=alkyloxycarbonyl, aryloxycarbonyl, aralkyloxycarbonyl, or an acyl group.
(iii) converting the compound obtained in step (ii) into the corresponding aldehyde by hydrolysis, transacetalization or hydrogenblysis of the acetal group, for obtaining the compound of the general formula (I) wherein R$_1$=CHO and R$_2$=alkyloxycarbonyl, aryloxycarbonyl, aralkyloxycarbonyl, or an acyl group.

11. A process as claimed in claim 10, wherein, in step (i) the inert solvent is selected from a group consisting essentially of an aprotic solvent, a halogenated solvent, an ether, and an aromatic hydrocarbon.

12. A process as claimed in claim 10, wherein, in step (i) and (ii) the organic base is selected from a group consisting essentially of a tertiary amine, an aromatic amine, a heterocyclic amine, a carbonate and a bicarbonate.

13. A process as claimed in claim 10, wherein, in step (ii) said reagent is selected from a group consisting essentially of a chloroformate; a dicarbonate; N-(benzyloxycarbonyloxy) succinimide; an acid chloride and an anhydride.

14. A process as claimed in claim 10, wherein, in step (ii) the inert solvent is selected from a group consisting essentially of a ketone, a halogenated derivative, an ester, an ether and an aprotic solvent.

15. A process as claimed in claim 10, characterized in that in step (iii) the hydrolysis reaction is carried out in an organic solvent in the presence of an at least stoichiometric amount of water, and an organic or inorganic acid.

16. A process as claimed in claim 10, characterized in that in step (iii) the transacetalization reaction is carried out in the presence of a ketone and an organic or inorganic acid.

17. A process as claimed in anyone of claim 15 or 16, wherein the reaction is performed in the presence of hydrochloric, sulfuric, methanesulfonic, p-toluenesulfonic or trifluoroacetic acid, at a temperature ranging from 15° C. to 50° C.

18. A process as claimed in claim 10, characterized in that in step (iii) the hydrogenolysis reaction is carried out in the presence of a catalyst in an inert solvent, at a temperature ranging from 10° C. to 50° C.

19. A process as claimed in claim 18, wherein the catalyst is palladium.

20. A process as claimed in claim 18, where in the solvent is selected form a group consisting essentially of a $C_1$ to a $C_4$ alcohol, an ester and an ether.

21. A process as claimed in claim 5 wherein said ether is one of an ethyl ether and a tetrahydrofuran.

22. A process as claimed in claim 11, wherein said aprotic solvent is one of N,N-dimethyl-formamide, N-methylpirrolidone or dimethylsulfoxide.

23. A process as claimed in claim 11, wherein said halogenated solvent is is one of methylene chloride and chloroform.

24. A process as claimed in claim 11, wherein said ether is one of tetrahydrofuran and dioxane.

25. A process as claimed in claim 11, wherein said aromatic hydrocarbon is one of benzene, toluene and xylene.

26. A process as claimed in claim 12, wherein said tertiary amine is one of triethylamine and diisopropylamine.

27. A process as claimed in claim 12, wherein said aromatic amine is N,N-dimethylaniline.

28. A process as claimed in claim 12, wherein hetrocyclic amine is pyridine.

29. A process as claimed in claim 13, wherein said chloroformate is one of ethyl chloroformate, tert-butyl chloroformate and benzyl chloroformate.

30. A process as claimed in claim 13, wherein said dicarbonate is one of di-tert-butyl dicarbonate and dibenzyl dicarbonate.

31. A process as claimed in claim 14, wherein said ketone is acetone.

32. A process as claimed in claim 14, wherein said halogenated derivative is one of methylene chloride and chloroform.

33. A process as claimed in claim 14, wherein said ester is ethyl acetate.

34. A process as claimed in claim 14, wherein said ether is one of tetrahydrofuran and dioxane.

35. A process as claimed in claim 14, wherein said aprotic solvent is one of N,N-dimethylacetamide and N,N-dimethylformamide.

36. A process as claimed in claim 20, wherein said $C_1$ to a $C_4$ alcohol is one of methanol, ethanol, isopropanol and butanol.

37. A process as claimed in claim 20, wherein said ester is ethyl acetate.

38. A process as claimed in claim 20, wherein said ether is tetrahydrofuran.

* * * * *

UNITED STATES PATENT AND TRADEMARK OFFICE
CERTIFICATE OF CORRECTION

PATENT NO. : 6,388,134 B1  Page 1 of 1
DATED : May 14, 2002
INVENTOR(S) : Jordi Bessa Bellmunt et al.

It is certified that error appears in the above-identified patent and that said Letters Patent is hereby corrected as shown below:

<u>Title page,</u>
Item [73], insert as follows:
-- [73]  Vita-Invest, S.A., Sant Joan Despi, Spain --

Signed and Sealed this

Fifteenth Day of October, 2002

*Attest:*

*Attesting Officer*

JAMES E. ROGAN
*Director of the United States Patent and Trademark Office*